US008017319B2

(12) United States Patent
Rigler

(10) Patent No.: US 8,017,319 B2
(45) Date of Patent: *Sep. 13, 2011

(54) EVANESCENCE-BASED MULTIPLEX SEQUENCING METHOD

(76) Inventor: Rudolf Rigler, St-Sulpice (CH)

( * ) Notice: Subject to any disclaimer, the term of this patent is extended or adjusted under 35 U.S.C. 154(b) by 545 days.

This patent is subject to a terminal disclaimer.

(21) Appl. No.: 10/499,547

(22) PCT Filed: Dec. 18, 2002

(86) PCT No.: PCT/EP02/14490
§ 371 (c)(1),
(2), (4) Date: Feb. 14, 2005

(87) PCT Pub. No.: WO03/052137
PCT Pub. Date: Jun. 26, 2003

(65) Prior Publication Data
US 2007/0020626 A1 Jan. 25, 2007

(30) Foreign Application Priority Data
Dec. 19, 2001 (DE) .................. 101 62 536

(51) Int. Cl.
*C12Q 1/68* (2006.01)
*C12M 1/00* (2006.01)
*C12M 1/34* (2006.01)
*C12M 3/00* (2006.01)
*G02B 6/10* (2006.01)
*C07H 21/02* (2006.01)
(52) U.S. Cl. ...... 435/6; 435/283.1; 435/287.2; 385/129; 536/23.1
(58) Field of Classification Search .................. 385/129; 435/6, 283.1, 287.2; 536/23.1
See application file for complete search history.

(56) References Cited

U.S. PATENT DOCUMENTS

| | | | | |
|---|---|---|---|---|
| 5,547,839 | A * | 8/1996 | Dower et al. ........... | 435/6 |
| 5,585,242 | A | 12/1996 | Bouma et al. | |
| 6,225,068 | B1 | 5/2001 | Wolfrum | |
| 6,232,075 | B1 * | 5/2001 | Williams ............... | 435/6 |
| 6,245,506 | B1 * | 6/2001 | Laugharn et al. ....... | 435/6 |
| 6,296,810 | B1 | 10/2001 | Ulmer | |
| 2001/0036629 | A1 | 11/2001 | Fodor et al. | |
| 2002/0042059 | A1 * | 4/2002 | Makarov et al. ........ | 435/6 |

FOREIGN PATENT DOCUMENTS

| | | |
|---|---|---|
| DE | 199 47 616 A | 5/2001 |
| WO | WO 02 02795 A | 1/2002 |

OTHER PUBLICATIONS

Sauer et al, Single molecule DNA sequencing in a submicrometer channels: state of the art and futhure prospects, 2001, J. Biotechnology, 86, 181-2001.*
Werner et al, Exonucleasel hydrolyzes DNA with a distribution of rates, 2005, Biophysical Journal 86, 1403-1412.*
Matsurura et al, Real time observation of single DNA digestion by lambda exonuclease under a fluorescence microscope filed, 2001, Nucleic acid reasearch, 29, e79.*
Bayley H, Sequencing single molecule of DNA, 2006, Current opinion in chemical biology,10, 628-637.*
Yu et al, Cyanine dye dUTP analogs for enzymatic labeling of DNA probes, 1994, Nucleic acids Research, 22, 3326-3232.*
Braslavsky et al, Sequence information can be obtained from single DNA molecules, 2003, Proc. Natl. Acad. Sci. USA,100, 3960-3964.*
Brakmann et al, A further step towards single molecule sequencing, 2002, Angew. Chem. Int. Ed. 41, 3215-3217).*
Werner et al, Progress towards single molecule DNA sequencing, 2003, Journal of Bacteriology, 101, 1-14.*
Sauer M. et al., "Single Molecule DNA Sequencing in Submicrometer Channels: State of the Art and Future Prospects." *Journal of Biotechnology*, 2001; pp. 181-201, vol. 86, Elsevier Science B.V., Germany.
Stephan J. et al. "Towards a General Procedure for Sequencing Single DNA Molecules"; *Journal of Biotechnology*, 2001. pp. 255-267, vol. 86, Elsevier Science B.V., Germany.
Lindsay S. M. & Philipp M., "Can the Scanning Tunneling Microscope Sequence DNA?" *Genetic Analysis, Techniques and Applications*, 1991. pp. 8-13, vol. 8, No. 1. Elsevier Science Publishing Co., Inc., New York, NY.
Huang et al., "DNA Sequencing Using Capillary Array Electrophoresis." *Analytical Chemistry*, Sep. 15, 1992. pp. 2149-2154, vol. 64, No. 18. American Chemical Society Publications, Washington, DC.
Kambara H. & Takahashi S., "Multiple-sheathflow Capillary Array DNA Analyser." *Nature*, Feb. 11, 1993. pp. 565-566, vol. 361. Nature Publishing Group. Tokyo, Japan.
Maskos U. & Southern E. M., "Parallel Analysis of Oligodeoxyribonucleotide (Oligonucleotide) Interactions. I. Analysis of Factors Incluencing Oligonucleotide Duplex Formation." *Nucleic Acids Research*, Apr. 11, 1992, pp. 1675-1678, vol. 20, No. 7. Oxford University Press, Oxford, UK.
Maskos U. & Southern E. M., "Oligonucleotide Hybridisations on Glass Supports: A Novel Linker for Oligonucleotide Synthesis and Hybridisation Properties of Oligonucleotides Synthesizes in situ." *Nucleic Acids Research*, 1992, pp. 1679-1684, vol. 20, No. 7. Oxford University Press, Oxford, UK.
Adams M. et al., "Automated DNA Sequencing and Analysis." 1994. Academic Press Limited. London, UK. Drmanac et al., "Sequencing of Megabase Plus DNA by Hybridization: Theory of the Method." *Genomics*, vol. 4, No. 2, Feb. 1989. pp. 114-128. Academic Press, San Diego, CA.
Hillenkamp et al., "Matrix-Assisted Laser Desorption/Ionization Mass Spectrometry of Biopolymers." *Analytical Chemistry*, vol. 63, No. 24, Dec. 15, 1991, pp. 1193A-1203A. American Chemical Society Publications, Washington, DC.
Sanger et al., "DNA sequencing with chain-terminating inhibitors." *Proceedings of the National Academy of Sciences*, vol. 74, No. 12, Dec. 1977. pp. 5463-5467. National Academy of Sciences, U.S.A.
Khrapko et al., "An oligonucleotide hybridization approach to DNA sequencing." *FEBS Letters*, Oct. 9, 1989, vol. 256, pp. 118-122, Elsevier Science B.V., Netherlands.
Dörre et al., "Techniques for Single Molecule Sequencing," *Bioimaging*, vol. 5, 1997. pp. 139-152.

* cited by examiner

*Primary Examiner* — Stephen Kapushoc
*Assistant Examiner* — Narayan Bhat
(74) *Attorney, Agent, or Firm* — The Webb Law Firm, PC

(57) ABSTRACT

The invention relates to a method and a device for evanescence-based multiplex sequencing of nucleic acid molecules immobilized on a support.

13 Claims, 3 Drawing Sheets

EVANESCENCE-BASED MULTIPLEX SEQUENCING METHOD

BACKGROUND OF THE INVENTION

1. Field of the Invention

The invention concerns a method and a device for an evanescence-based multiplex sequencing of nucleic acid molecules immobilized on a support.

2. Description of the Prior Art

The sequencing of the human genome consisting of about $3\times10^9$ bases or of the genome of other organisms as well as the determination and comparison of individual sequence variants requires the provision of sequencing methods that are rapid and can also be used routinely and inexpensively. Although major attempts have been made to accelerate conventional sequencing methods such as the enzymatic chain termination method of Sanger et al. (Proc. Natl. Acad. Sci. USA 74 (1977) 5463) especially by automation (Adams et al. Automated DNA Sequencing and Analysis (1994), New York, Academic Press), at present no more than 2000 bases per day can be determined with a sequencer.

New approaches for overcoming the limitations of conventional sequencing methods have been developed in the last few years which include sequencing by scanning-tunnel microscopy (Lindsay and Phillip, Gen. Anal. Tech. Appl. 8 (1991), 8-13), by highly parallelized capillary electrophoresis (Huang et al., Anal. Chem. 64 (1992), 2149-2154; Kambara and Takahashi, Nature 361 (1993), 565-566), by oligonucleotide hybridization (Drmanac et al., Genomics 4 (1989), 114-128; Khrapko et al., FEBS Let. 256 (1989), 118-122; Maskos and Southern, Nucleic Acids Res. 20 (1992), 1675-1678 and 1679-1684) and by matrix-assisted laser desorption/ionization mass spectroscopy (Hillenkamp et al., Anal. Chem. 63 (1991), 1193A-1203A).

Another method is single molecule sequencing (Dörre et al., Bioimaging 5 (1997), 139-152) in which nucleic acids are sequenced by progressive enzymatic degradation of fluorescent-labelled single-stranded DNA molecules and detection of the sequentially released monomer molecules in a microstructure channel. The advantage of this method is that only a single molecule of the target nucleic acid is sufficient to carry out a sequence determination.

Although considerable advances have been made by using the above-mentioned methods, there is a major need for further improvements. Hence the object of the present invention was to provide a method for sequencing nucleic acids which represents a further improvement over the prior art and which allows a parallel determination of individual nucleic acid molecules in a multiplex format.

A multiplex sequencing method is proposed in PCT/EP01/07462 in which nucleic acid molecules that carry several fluorescent marker groups are provided in an immobilized form on a support and the base sequence of several nucleic acid molecules is determined simultaneously on the basis of the time-dependent change in the fluorescence of the nucleic acid molecules or/and of the cleaved nucleotide building blocks caused by the cleavage of nucleotide building blocks.

SUMMARY OF THE INVENTION

The subject matter of the present application is a method for sequencing nucleic acids comprising the steps:
(a) providing an at least partially optically transparent support with a multitude nucleic acid molecules immobilized thereon where the nucleic acid molecules carry several fluorescent marker groups,
(b) progressive cleavage of individual nucleotide building blocks from the immobilized nucleic acid molecules and
(c) simultaneous determination of the base sequence of a plurality of nucleic acid molecules based on the time-dependent change in the fluorescence of the nucleic acid molecules or/and of the cleaved nucleotide building blocks caused by the cleavage of nucleotide building blocks, wherein the fluorescence is produced by beaming light into the support and generating an evanescent excitation field by internal reflection at the support surface in the area of the immobilized nucleic acid molecules.

Yet another subject matter of the invention is a device for sequencing nucleic acids comprising:
(a) an at least partially optically transparent support comprising a multitude of nucleic acid molecules immobilized thereon where the nucleic acid molecules are present in a single-stranded form and carry several fluorescent marker groups,
(b) a reaction space for the progressive cleavage of individual nucleotide building blocks from the immobilized nucleic acid molecules,
(c) means for exciting fluorescence by beaming light into the support and generating an evanescent excitation field by internal reflection at the support surface in the area of the immobilized nucleic acid molecules, and
(d) means for simultaneously determining the base sequence of a plurality of nucleic acid molecules based on the time-dependent change in fluorescence of the nucleic acid molecules or/and of the cleaved nucleotide building blocks caused by cleavage of nucleotide building blocks.

The method according to the invention and the device according to the invention can be used for example to analyse genomes and transcriptomes or for differential analyses e.g. investigations of differences in the genome or transcriptome of individual species or organisms within a species.

DETAILED DESCRIPTION OF THE PREFERRED EMBODIMENTS

Figure 1:
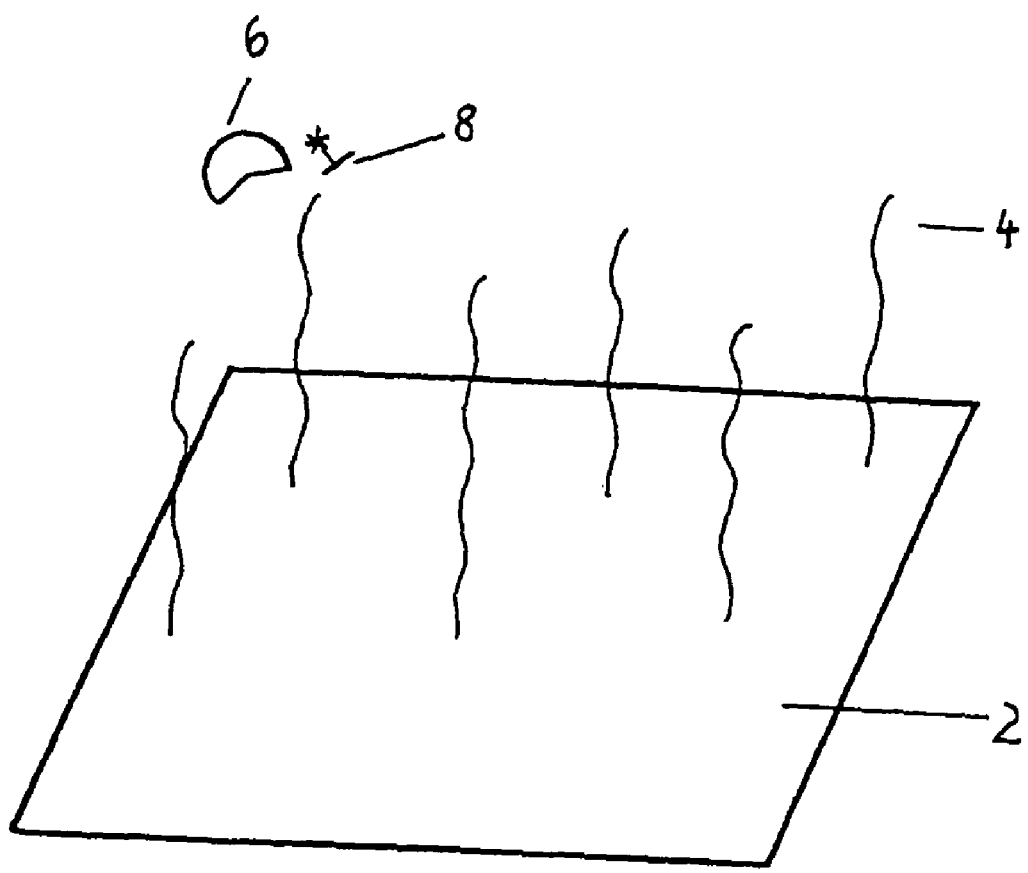
FIG. 1 is a schematic view of an optically transparent support, according to the invention.

The method according to the invention is a support-based multiplex sequencing method in which a multitude of immobilized nucleic acid molecules are examined simultaneously. The support used for the method can be any desired planar or structured support that is suitable for immobilizing nucleic acid molecules and has, at least in the area of the immobilized nucleic acids sufficient optical transparency and suitable surface properties for an evanescence-based detection of fluorescence. Examples of suitable support materials are glass, quartz, plastic or composite materials containing these materials. In principle the support can be designed in any manner, provided a reaction space can be formed which allows the progressive cleavage of individual nucleotide building blocks from nucleic acids immobilized on the support in a liquid reaction mixture.

The nucleic acid molecules that can be in a single-stranded form or in a double stranded form are preferably immobilized on the support via their 5' or 3' ends. In the case of double-stranded molecules it must be ensured that labelled nucleotide building blocks can only be cleaved from a single strand. The nucleic acid molecules can be bound to the support by means of covalent or non-covalent interactions. For example the binding of polynucleotides to the support can be mediated by high affinity interactions between the partners of a specific binding pair, e.g. for example mediated by biotin/streptavidin or avidin, hapten/anti-hapten-antibody, sugar/lectin etc. Thus biotinylated nucleic acid molecules can be coupled to streptavidin-coated supports. Alternatively the nucleic acid molecules can also be adsorptively bound to the support. Hence nucleic acid molecules modified by incorporation of alkanethiol groups can be bound to metallic supports e.g. gold supports. Another alternative is covalent immobilization in which the binding of the polynucleotides can be mediated by reactive silane groups on a silica surface.

A plurality of nucleic acid molecules that are to be sequenced are bound to a support. Preferably at least 100, particularly preferably at least 1,000 and especially preferably at least 10,000 and up to more than $10^6$ nucleic acid molecules are bound to the support. The bound nucleic acid fragments have a length of preferably 200 to 2,000 nucleotides, particularly preferably 400 to 1,000 nucleotides. The nucleic acid molecules bound to the support, e.g. DNA molecules or RNA molecules, contain a plurality of fluorescent marker groups and preferably at least 50%, particularly preferably at least 70% and most preferably essentially all, e.g. at least 90%, of the nucleotide building blocks of one base type carry a fluorescent marker group. Nucleic acids labelled in this manner can be produced by enzymatic primer extension on a nucleic acid template using a suitable polymerase e.g. a DNA polymerase such as Taq polymerase, a thermostable DNA polymerase from *Thermococcus gorgonarius* or other thermostable organisms (Hopfner et al., PNAS USA 96 (1999), 3600-3605) or a mutated Taq polymerase (Patel and Loeb, PNAS USA 97 (2000), 5095-5100) using fluorescent-labelled nucleotide building blocks.

The labelled nucleic acid molecules can also be produced by amplification reactions e.g. PCR. Thus in an asymmetric PCR, amplification products are formed in which only a single strand contains fluorescent labels. Such asymmetric amplification products can be sequenced in a double-stranded form. Nucleic acid fragments are formed by symmetrical PCR in which both strands are fluorescent labelled. These two fluorescent labelled strands can be separated and immobilized separately in a single-stranded form so that the sequence of one or both complementary strands can be determined separately. Alternatively one of the two strands can be modified at the 3' end for example by incorporation of a PNA clip, such that monomer building blocks can no longer be cleaved off. In this case double-strand sequencing is possible.

Preferably essentially all nucleotide building blocks of at least two base types, for example two, three of four base types, carry a fluorescent label and each base type advantageously carries a different fluorescent marker group. If the nucleic acid molecules are not completely labelled, the sequence can nevertheless be completely determined by sequencing a plurality of molecules in parallel.

The nucleic acid template whose sequence is to be determined, can for example be selected from DNA templates such as genomic DNA fragments, cDNA molecules, plasmids etc. and also from RNA templates such as mRNA molecules.

The fluorescent marker groups can be selected from known fluorescent marker groups used to label biopolymers e.g. nucleic acids such as fluorescein, rhodamine, phycoerythrin, Cy3, Cy5 or derivatives thereof etc.

The method according to the invention is based on the fact that fluorescent marker groups incorporated into nucleic acid strands interact with neighbouring groups, for example with chemical groups of the nucleic acids and in particular with nucleobases such as G, or/and with adjacent fluorescent marker groups which results in a change in the fluorescence and in particular in the fluorescence intensity compared to that of the fluorescent marker groups in an isolated form due to quenching or/and energy transfer processes. Cleavage of individual nucleotide building blocks results in a change in the total fluorescence e.g. the fluorescence intensity of an immobilized nucleic acid strand is changed in a manner depending on the cleavage of individual nucleotide building blocks i.e. as a function of time. This change in the fluorescence over time can be detected in parallel for a plurality of nucleic acid molecules and can be correlated with the base sequence of individual nucleic acid strands. Fluorescent marker groups are preferably used which are at least partially quenched when they are incorporated into the nucleic acid strand such that after cleavage of the nucleotide building block containing the marker group or of a neighbouring building block which causes the quenching, the fluorescence intensity is increased.

The sequencing reaction of the method according to the invention comprises the progressive cleavage of individual nucleotide building blocks from the immobilized nucleic acid molecules. An enzymatic cleavage is preferably carried out using an exonuclease in which single strand or double strand exonucleases that degrade in the 5'→3' direction or 3'→5' direction can be used depending on the manner in which the nucleic acid strands are immobilized on the support. T7 DNA polymerase, *E. coli* exonuclease I or *E. coli* exonuclease III are particularly preferably used as exonucleases.

A change in the fluorescence intensity of the immobilized nucleic acid strand or/and of the cleaved nucleotide building blocks due to quenching or energy transfer processes can be measured during the progressive cleavage of individual nucleotide building blocks. This change in the fluorescence intensity over time depends on the base sequence of the examined nucleic acid strand and can therefore be correlated with the sequence. In order to completely determine the sequence of a nucleic acid strand, several nucleic acid strands labelled on different bases e.g. A, G, C and T or combinations of two different bases are preferably generated by enzymatic primer extension as described above and immobilized on the support where the immobilization can be at random sites on the support or can be carried out in a site-specific manner. A sequence identifier may optionally also be attached to the nucleic acid strand to be examined e.g. a labelled nucleic acid of a known sequence, for example by means of an enzymatic reaction using ligase or/and terminal transferase such that firstly a known fluorescence pattern is obtained at the start of the sequencing and the fluorescence pattern of the unknown sequence to be examined is only obtained afterwards. Preferably a total of $10^3$ to $10^6$ nucleic acid strands are immobilized on a support.

In order to accelerate the removal of cleaved nucleotide building blocks from the immobilized nucleotide strands, a convection flow is preferably generated in the reaction space away from the support. The flow rate can be in the range of 1 to 10 mm/s.

The detection comprises beaming light into the support preferably by means of a laser. One or several laser beams can be used for this e.g. a widened laser beam with a cross-section of ca. 1-20 mm or/and multiple laser beams. An evanescent excitation field is generated by internal reflection at one or more positions of the support surface in the area of immobilized nucleic acid molecules which excites the fluorescent marker groups on the nucleic acid molecules immobilized on the support. The reflection on the support surface is preferably a total internal reflection.

The fluorescence emission of a plurality of nucleic acid strands generated by evanescent excitation can be detected in parallel using a detector matrix which for example comprises an electronic detection matrix e.g. a CCD camera or an avalanche photodiode matrix. Detection can be such that fluorescence excitation and detection occurs concurrently on all examined nucleic acid strands. Alternatively the nucleic acid strands can be examined portion by portion in several steps. It is preferable to detect the fluorescence light that is irradiated essentially orthogonally from the support surface.

The present invention is further elucidated by the following figures.

FIG. 1 shows a schematic representation of an optically transparent support (2) according to the invention with a multitude of single-stranded labelled nucleic acid molecules (4) immobilized thereon. A support with an area of 1 to 2 cm$^2$ can for example contain up to 10$^6$ nucleic acid strands.

Figure 2:
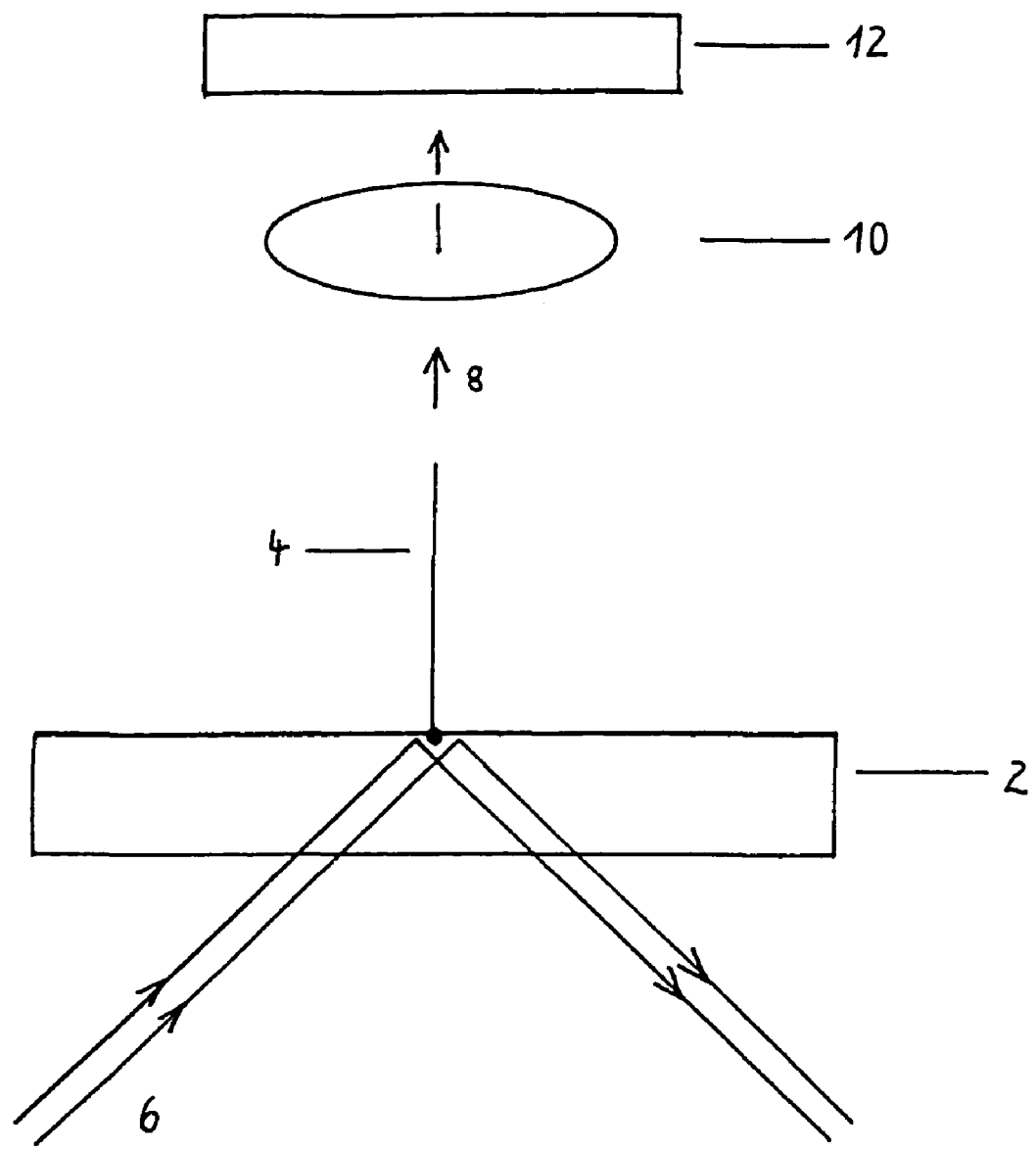
FIG. 2 is a schematic view showing excitation light beamed into the optically transparent support of FIG. 1.

FIG. 2 shows a first embodiment of the invention in which excitation light (6) is beamed into the optically transparent support (2) with nucleic acid molecules (4) immobilized thereon by a widened laser and the light emerges again from the support (2) after reflection at the glass surface in the area of the immobilized nucleic acid molecules (4). The immobilized nucleic acid molecules (4) are excited to fluoresce by the evanescent excitation field. The emission light (8) is guided by an optical system (10) onto a detector (12).

Figure 3:
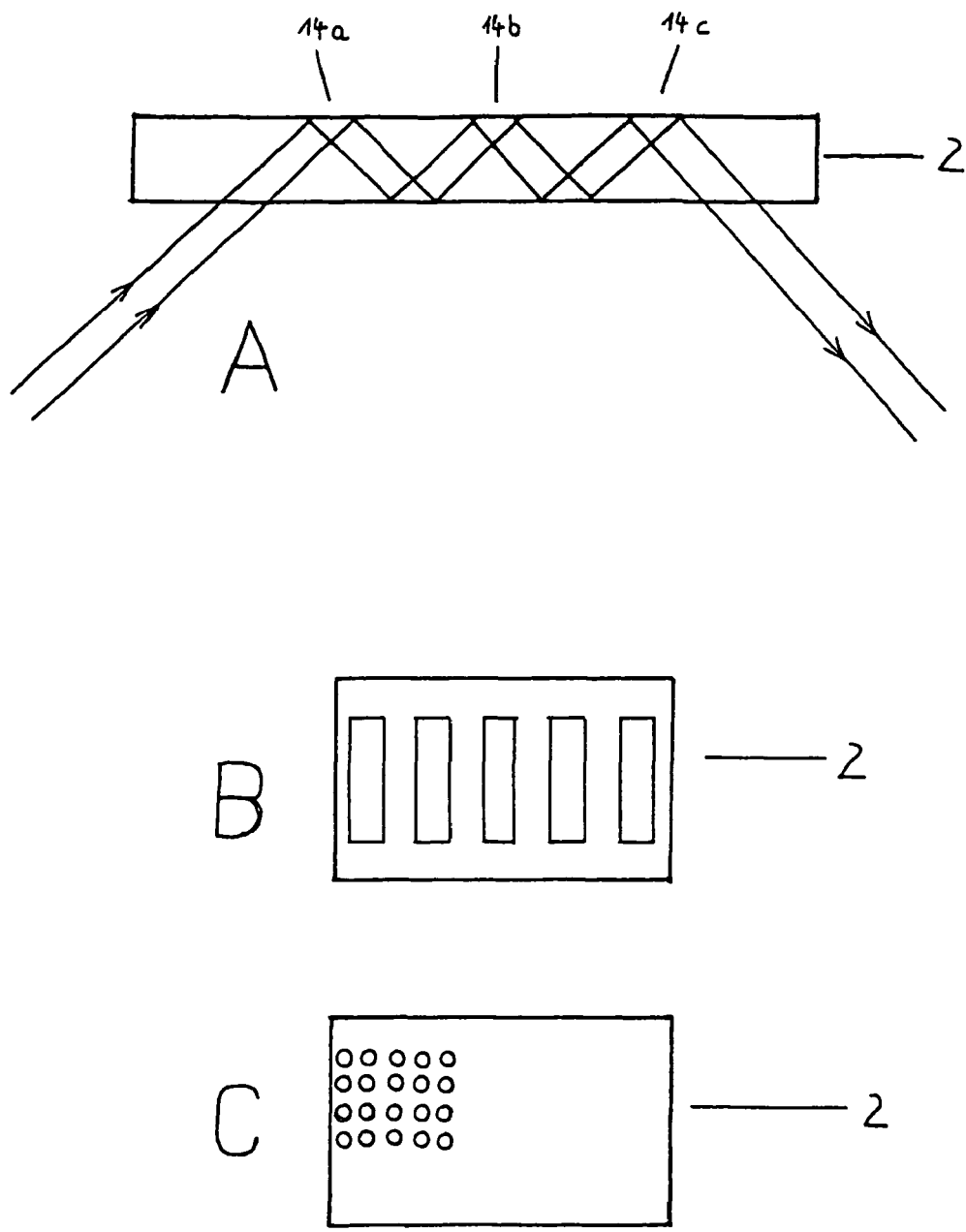
FIG. 3A is a schematic view showing evanescent excitation fields generated by multiple reflections in the optically transparent support of FIG. 1.
FIG. 3B is a schematic view showing evanescent excitation fields in the form of strips.
FIG. 3C is a schematic view showing evanescent excitation fields in the form of points.

In the embodiment shown in FIG. 3A evanescent excitation fields are generated by multiple reflections (14a, 14b, 14c) in the optically transparent support (2). The evanescent excitation fields can for example be present in the form of strips (FIG. 3B) or points (FIG. 3C).

Alternatively it is also possible to beam several foci of the laser light into the support by using a diffractive optical system such as that disclosed in DE 101 26 083.0.

The advantages achieved by the method according to the invention and the device according to the invention are in particular that fluorescence excitation and measurement can take place on different sides. This results in lower background radiation and thus a higher measuring sensitivity.

The invention claimed is:

1. Method for sequencing nucleic acids comprising the steps:
   (a) providing an at least partially optically transparent support with a multitude of identical nucleic acid molecules immobilized thereon wherein the nucleic acid molecules carry several fluorescent marker groups,
   (b) progressive cleavage of individual nucleotide building blocks from the immobilized identical nucleic acid molecules, and
   (c) simultaneous determination of the base sequence of the plurality of nucleic acid molecules based on a time-dependent change in the fluorescence of the nucleic acid molecules and the time-dependent change in the fluorescence of the cleaved nucleotide building blocks caused by the cleavage of nucleotide building blocks, wherein the fluorescence is produced by beaming light into the support and generating an evanescent excitation field by internal reflection at the support surface in the area of the immobilized nucleic acid molecules, wherein the molecule sequencing is single molecule sequencing, wherein the cleavage of said multitude of individual nucleotide building blocks from a plurality of single immobilized nucleic acid molecules is measured and carried out in one single step by using a reagent selected from the group consisting of a single strand-specific exonuclease and a double strand-specific exonuclease, and wherein each nucleic acid molecule is measured separately and the measurements of each individual nucleic acid molecule are carried out in parallel by means of a detection matrix.

2. Method as claimed in claim 1, wherein a support made of glass, plastics, quartz or a composite containing one or more of these materials is used.

3. Method as claimed in claim 1, wherein a total internal reflection is generated at the support surface.

4. Method as claimed in claim 1, wherein the nucleic acid molecules are labelled in such a manner that at least 50% of all nucleotide building blocks of one base type carry a fluorescent marker group.

5. Method as claimed in claim 4, wherein essentially all nucleotide building blocks of one base type carry a fluorescent marker group.

6. Method as claimed in claim 1, wherein the exonuclease is selected from the group consisting of T7 DNA polymerase, *E. coli* exonuclease I and *E. coli* exonuclease III.

7. Method as claimed in claim 1, wherein the evanescent field is generated by beaming in light using a widened laser.

8. Method as claimed in claim 1, wherein the evanescent field is generated at multiple areas on the support by irradiating it with multiple laser beams or/and by means of multiple internal reflections.

9. Method as claimed in claim 1, wherein the detection matrix includes an electronic matrix selected from the group consisting of a CCD camera and an avalanche photodiode matrix.

10. Method as claimed in claim 1, wherein the fluorescence excitation and detection is carried out in several steps and in each case on a portion of the nucleic acid strands to be examined.

11. Method as claimed in claim 1, wherein a convection flow away from the support is generated during the determination.

12. Method as claimed in claim 1, wherein the fluorescent marker groups are at least partially quenched when they are incorporated into the nucleic acid strands and the fluorescence intensity is increased after cleavage.

13. Method as claimed in claim 1, wherein the cleavage of said multitude of individual nucleotide building blocks from a plurality of single immobilized nucleic acid molecules is measured and carried out in one single step by using a single nucleic acid strand which is digested and a single strand-specific exonuclease reagent.

* * * * *